(12) United States Patent
Bowers (10) Patent No.: US 12,036,345 B2
(45) Date of Patent: Jul. 16, 2024

(54) BLOOD PROCESSING SYSTEM

(71) Applicant: Spectrum Medical Ltd, Gloucester (GB)

(72) Inventor: Scott Bowers, Gloucester (GB)

(73) Assignee: SPECTRUM MEDICAL LTD, Gloucester (GB)

(*) Notice: Subject to any disclaimer, the term of this patent is extended or adjusted under 35 U.S.C. 154(b) by 886 days.

(21) Appl. No.: 17/054,792

(22) PCT Filed: May 21, 2019

(86) PCT No.: PCT/GB2019/051403
§ 371 (c)(1),
(2) Date: Nov. 12, 2020

(87) PCT Pub. No.: WO2019/224533
PCT Pub. Date: Nov. 28, 2019

(65) Prior Publication Data
US 2021/0369931 A1    Dec. 2, 2021

(30) Foreign Application Priority Data

May 22, 2018  (GB) ..................................... 1808381

(51) Int. Cl.
*A61M 1/16* (2006.01)

(52) U.S. Cl.
CPC ... *A61M 1/1698* (2013.01); *A61M 2202/0225* (2013.01); *A61M 2205/3334* (2013.01);
(Continued)

(58) Field of Classification Search
CPC .............. A61M 1/1621; A61M 1/1698; A61M 1/3621; A61M 2202/0225;
(Continued)

(56) References Cited

U.S. PATENT DOCUMENTS

| | | | |
|---|---|---|---|
| 6,004,511 A | 12/1999 | Biscegli | |
| 2014/0216252 A1* | 8/2014 | Joost | A61M 1/1698 96/6 |

(Continued)

FOREIGN PATENT DOCUMENTS

| | | |
|---|---|---|
| GB | 2437254 | 10/2007 |
| JP | 2010213851 A | 9/2010 |

(Continued)

OTHER PUBLICATIONS

International Search Report and Written Opinion for corresponding PCT Application No. PCT/GB2019/051403, mailed on Jun. 29, 2019—10 pages.

(Continued)

*Primary Examiner* — Benjamin J Klein
(74) *Attorney, Agent, or Firm* — Dority & Manning, P.A.

(57) ABSTRACT

A blood gas management device comprises a blood passage having a gas-blood interface with a plurality of gas passages, and is arranged to direct a flow of supply gas from the gas inlets through the gas passages to the gas outlets, and to allow a flow of blood in a blood flow path through the blood passage to thereby permit an exchange of blood gas with the supply gas via the interface. The blood gas management device comprises a supply gas distribution arrangement allowing the supply gas to be provided from different directions relative to the blood flow path. This provides an improved gas-transfer gradient at different locations along the gas passage.

20 Claims, 4 Drawing Sheets

(52) U.S. Cl.
CPC ... *A61M 2230/20* (2013.01); *A61M 2230/202* (2013.01); *A61M 2230/205* (2013.01)

(58) Field of Classification Search
CPC .... A61M 2205/3334; A61M 2230/202; A61M 2230/205
See application file for complete search history.

(56) References Cited

U.S. PATENT DOCUMENTS

| | | | | |
|---|---|---|---|---|
| 2016/0015881 | A1* | 1/2016 | Utsugida | A61M 1/3666 422/48 |
| 2019/0160217 | A1* | 5/2019 | Marseille | B01D 63/026 |

FOREIGN PATENT DOCUMENTS

| | | |
|---|---|---|
| JP | 2018500972 A | 1/2018 |
| WO | WO2005/118025 | 12/2005 |
| WO | WO 2008/107723 | 9/2008 |
| WO | WO 2017/211460 | 12/2017 |

OTHER PUBLICATIONS

Search Report for corresponding GB Application No. GB1808381.6, dated Nov. 19, 2018—4 pages.

Japanese Office Action (w/ English translation) for corresponding JP Application No. 2020-564602, dated Mar. 28, 2023, 12 pages.

International Preliminary Report on Patentability for corresponding PCT Application No. PCT/GB2019/051403, issued on Nov. 24, 2020—8 pages.

* cited by examiner

PRIOR ART

Fig. 1

PRIOR ART

| 52 | Provide a blood treatment device with a gas-blood interface with a bi- or multi-directional gas supply |

| 54 | Supply gas in at least two directions |

| 56 | Modulate supply gas differently for each direction |

| 58 | Modulate area of gas-blood interface region(s) |

| 60 | Monitor a blood gas value of outgoing blood |

| 62 | Modulate supply gas flow rate |

| 64 | Modulate supply gas composition |

Fig. 6

BLOOD PROCESSING SYSTEM

PRIORITY CLAIM

This application is a national stage application, filed under 35 U.S.C. § 371, of International Patent Application No. PCT/GB2019/051403, filed on May 21, 2019, which claims the benefit of priority of Great Britain Patent Application No. 1808381.6, filed on May 22, 2018, both of which are incorporated by reference herein in their entirety.

FIELD OF THE INVENTION

The present invention relates to a blood treatment device and method. In particular, the present invention relates to a system and to a method for removing carbon dioxide from blood in systems that bypass the lung, such as extracorporeal blood oxygenation and carbon dioxide control.

BACKGROUND

Blood gas treatment devices, such as extracorporeal membrane oxygenators, allow a blood gas composition to be modulated by exposing blood to a supply gas via a gas-blood interface. The gas-blood interface may be provided in the form of gas-permeable walls of hollow fibres, wherein gas passes through the interior lumen of the hollow fibres and blood flows across the outside of the hollow fibres. Gas exchange across the gas-permeable walls is encouraged by a partial pressure gradient of relative partial pressures between the blood gas the supply gas. After the gas exchange, the supplied gas is removed as exhaust gas.

In extracorporeal membrane oxygenation, the partial pressure of oxygen in the outgoing blood (outgoing blood being the blood leaving the blood gas treatment device) is controllable by adjusting the composition of the supply gas. The partial pressure of carbon dioxide in the outgoing blood is controllable by adjusting the flow rate of the supply gas past the gas blood interface.

International patent application PCT/GB2015/053694 by the present applicant, published as WO2016/087859, the contents of which are incorporated by reference, discloses an oxygenation system with a flow control arrangement for controlling the flow rate of the exhaust gas relative to the supply gas. WO2016/087859 also discloses a blender for preparing a supply gas with a high-accuracy oxygen content at low flow rates. The blender and flow control arrangement disclosed in WO2016/087859 can be used to maintain low flow rates of a supply gas while also permitting a high degree of blending accuracy and while permitting exhaust gas to be withdrawn at an appropriate flow rate that is low, yet higher than the oxygenation gas supply. A system like WO2016/087859 allows a simultaneous modulation of the partial pressure of oxygen and carbon dioxide in the outgoing blood.

The present invention seeks to provide further improvements over existing blood gas exchange devices.

SUMMARY OF THE INVENTION

In accordance with a first aspect of the invention, there is provided a blood gas management device as defined by claim 1. The blood gas management device comprises a plurality of gas passages each comprising a gas inlet and a gas outlet, and a blood passage arranged with a gas-blood interface with the gas passages. The blood gas management device is arranged to allow a flow of supply gas from the gas inlets through the gas passages to the gas outlets, and to allow a flow of blood in a blood flow path through the blood passage to thereby permit an exchange of blood gas with the supply gas via the gas-blood interface. The blood gas management device comprises a supply gas distribution arrangement allowing the supply gas to be provided to the gas-blood interface from different directions relative to the blood flow path.

The layout of a blood gas management device can be visualised as a plurality of gas passages (for instance, several thousands of hollow fibres) between a gas inlet and leading through to a gas exhaust. Blood is allowed to flow across the outside of the gas passages.

The present mechanism is based on the appreciation that the majority of carbon dioxide movement out of the blood and into the exhaust gas occurs relatively early in the gas-blood interface. The gas exchange is driven by the differential of the partial pressures of carbon dioxide in the blood and in the gas passage. In the present specification, the expression "gradient" may be used to refer to the differential. Due to the mobility of carbon dioxide, the differential decreases quickly along the gas passage. Therefore, fairly soon along the gas passage, the differential and, therefore, the gradient driving the gas transfer is reduced.

In existing systems, the carbon dioxide exchange can be modulated by changing the gas flow rate. By way of illustration, an increased gas flow rate achieves that more "fresh" supply gas is transported further into the gas passage per unit time. However, a limit is placed on gas flow modulation by practical considerations, such as maintaining a defined gas exchange of other gas components such as oxygen.

The present mechanism provides a better gas-transfer gradient over the length of the gas passage. The better gas-transfer gradient is achieved by supplying gas from different directions relative to the blood flow path. This allows fresh supply gas, with a higher differential of partial pressures of a relevant gas component, to be directed towards blood in downstream regions of the gas passage. By "fresh" supply gas, a supply gas is meant that has not yet been exposed to the blood in the gas-blood interface.

The gas supply from different directions may be a bi-directional or multi-directional gas supply, in which gas is supplied along two or more different directions relative to the blood flow path, in particular through the gas-blood interface. The gas supply may be ambi-directional with two or more gas passages arranged in counter flow relative to the flow of blood.

In some embodiments, the supply gas distribution arrangement is configured to provide a first supply of gas to cross at least part or all the blood flow path in a first direction and to provide a second supply of gas to cross at least part or all the blood flow path in a second direction different from the first direction.

The first and second supply may be of the same composition or of different composition. The first and second supply may have the same flow rate or different flow rates.

In some embodiments, at least one gas passage comprises a gas inlet in the direction of the gas outlets of another gas passage, whereby the at least one gas passage is configured to direct gas in counter flow to the other gas passage.

A counter flow arrangement allows the invention to be implemented with parallel gas passages. This may facilitate the construction of a blood gas management device. For instance, this may facilitate the design of the gas supplies.

In some embodiments, at least two or more multidirectional gas passages are arranged in series relative to the blood flow path.

By an arrangement in series it is meant that, in the direction of the blood flow, a first gas passage crosses the blood upstream of a second gas passage. Thereby, blood flowing across the gas passages is exposed to the first gas passage before being exposed to the second gas passage.

In some embodiments, the blood gas management device further comprises an exhaust removal system configured to extract exhaust gas from gas outlets in different directions relative to the flow of blood.

The exhaust gas removal system may be configured as described in WO2016/087859. The exhaust gas removal system may allow the exhaust gas flow rate of a gas passage to be modulated relative to the supply gas flow rate of the gas passage. For instance, the exhaust gas flow rate may be modulated, by way of a closed loop control, to match or exceed the supply gas flow rate.

In some embodiments, the exhaust gas removal system comprises a common connection to different gas outlets of multidirectional gas passages.

The exhaust gas removal system may be assisted by a vacuum or other suitable low-pressure source. The exhaust gas removal system may comprise auxiliary vents in the exhaust compartments of the gas passage. The auxiliary vents provide a safe-guard mechanism against over pressurisation at the gas-blood interface.

In some embodiments, at least some or all of the gas passages are provided by hollow fibres comprising gas-permeable walls.

It will be understood that the gas-permeability refers to the wall of the hollow fibre to allow gas exchange from the inside of the fibre, supplied by gas, across the wall to the outside of the fibre, where blood is allowed to flow.

In some embodiments, the blood gas management device is comprised in an extracorporeal oxygenator with a gas chamber at each end of the gas passages, wherein each gas chamber is separated into a plurality of compartments, each compartment allowing gas to be directed via a separate group of gas passages.

Existing oxygenator designs have a defined gas passage with an inlet zone and an exhaust zone. For example, a hollow-fibre oxygenator, which is a common oxygenator design, comprises many thousand hollow fibres each providing a gas passage from an inlet to an exhaust. One end of each fibre leads into a gas inlet zone and the other end of each fibre leads into a gas exhaust zone. The present invention is based on the appreciation that such known hollow fibre designs may be modified by supplying at least some gas in counter flow, i.e. a portion of the gas is supplied in a direction from what would conventionally be the gas exhaust zone towards what would conventionally be the gas inlet zone.

A gas chamber may be separated into a plurality of compartments by one or more partitions, each section having a border with a different region of the gas-blood interface.

In some embodiments, the blood gas management device comprises a gas sensor arrangement configured to obtain at least one gas value of a supply gas entering the gas inlet and/or exiting the gas outlet, wherein the at least one gas value comprises a gas flow rate, a gas pressure, and/or the percentage of carbon dioxide, oxygen, nitrogen, and/or a combination thereof.

In some embodiments, the blood gas management device comprises a blood sensor arrangement configured to obtain at least one blood value of the blood entering and/or exiting the gas-blood interface, wherein the at least one blood value comprises a blood flow rate, blood pressure, blood temperature, and/or the percentage of carbon dioxide, oxygen, nitrogen, and/or a combination thereof.

In some embodiments, the blood gas management device comprises a supply gas control system configured to receive as input one or more blood values or one or more gas values to modulate at least one gas flow parameter in response to the gas value and/or the blood value, wherein the at least one gas flow parameter comprises a composition and/or a flow rate of the supply gas.

The above-mentioned sensor arrangements and control system arrangements may be part of a blood gas management control system. The arrangements may be operationally linked with the blood gas management device and may be located outside the device's housing.

The supply of the gas through the multi-directional gas passages may be modulated in terms of gas composition and/or gas flow rate. Together with a sensor arrangement and control system this provides a closed loop control, or a feedback loop, that facilitates automatically modulating the blood gas value towards a set value or towards a target value.

Sensors, operationally linked with a mechanism controlling the flow rate and/or composition of the gas and or blood, respectively, allow a closed loop control to modulate the supply gas and/or blood stream to maintain a specific property, such as $PaO_2$, $PaCO_2$, and/or temperature, at a predetermined set point.

By "maintaining" a property, it is meant that the system is responsive to compensate gas parameters (flow, composition) to thereby compensate for temporary fluctuations about the predetermined set point.

For instance, a sensor may record that the blood carbon dioxide of blood having crossed a first number of fibres with a gas supply in a first direction and a second number of fibres with a gas supply in a second direction is not low enough, relative to a target carbon dioxide level. A control system may determine that the carbon dioxide level in the outgoing blood cannot be lowered by altering the gas flow rate of the first gas supply, for instance because this would undesirably affect the oxygenation performance. The blood gas management device may in that case modulate the flow rate and/or composition of the gas supply in the second direction to further reduce the blood carbon dioxide value, to avoid modulating the first gas supply.

In accordance with a second aspect of the invention, there is provided a method of using a blood gas management device as defined by claim 12. The blood gas management device comprises a plurality of gas passages each comprising a gas inlet and a gas outlet, and a blood passage having a gas-blood interface with the gas passages. The method comprises the steps of: directing a flow of supply gas from the gas inlets through the gas passages to the gas outlets, and allowing a flow of blood in a blood flow path through the blood passage to thereby permit an exchange of blood gas with the supply gas via the interface. The method further comprises providing the supply gas to the gas-blood interface from different directions relative to the blood flow path.

In some embodiments, the method comprises providing a first supply of gas to cross at least part or all the blood flow path in a first direction and providing a second supply of gas to cross at least part or all the blood flow path in a second direction different from the first direction, and optionally providing the second supply of gas in counter flow to the first supply of gas.

In some embodiments, the method comprises providing at least two or more multidirectional gas passages in series relative to the blood flow path.

In some embodiments, the method comprises extracting exhaust gas from gas outlets in different directions relative to the flow of blood, and optionally extracting the exhaust gas using a common exhaust gas removal system connected to different gas outlets of multidirectional gas passages.

In some embodiments, the method is used in an extracorporeal oxygenator with a gas chamber at each end of the gas passages, wherein each gas chamber is separated into a plurality of compartments, wherein the method comprises directing different supplies of gas via a separate group of gas passages.

In some embodiments, the method comprises using a gas sensor arrangement to obtain at least one gas value of a supply gas entering the gas inlet and/or exiting the gas outlet, wherein the at least one gas value comprises carbon dioxide, oxygen, nitrogen, and/or a combination thereof.

In some embodiments, the method comprises a blood sensor arrangement configured to obtain at least one blood value of the blood entering and/or exiting the gas-blood interface, wherein the at least one blood value comprises carbon dioxide, oxygen, nitrogen, or a combination thereof.

In some embodiments, the method comprises using a feedback loop to modulate at least one gas flow parameter in response to the gas value and/or the blood value, wherein the at least one gas flow parameter comprises a composition and/or a flow rate of the supply gas.

In some embodiments of the blood gas management device or of the method the plurality of gas passages is part of an oxygenator or of a carbon dioxide management device.

Optionally, the oxygenator or the device is an extracorporeal device, a wearable device, or an implantable device.

DESCRIPTION OF THE FIGURES

Exemplary embodiments of the invention will now be described with reference to the Figures, in which.

DESCRIPTION

Figure 1:
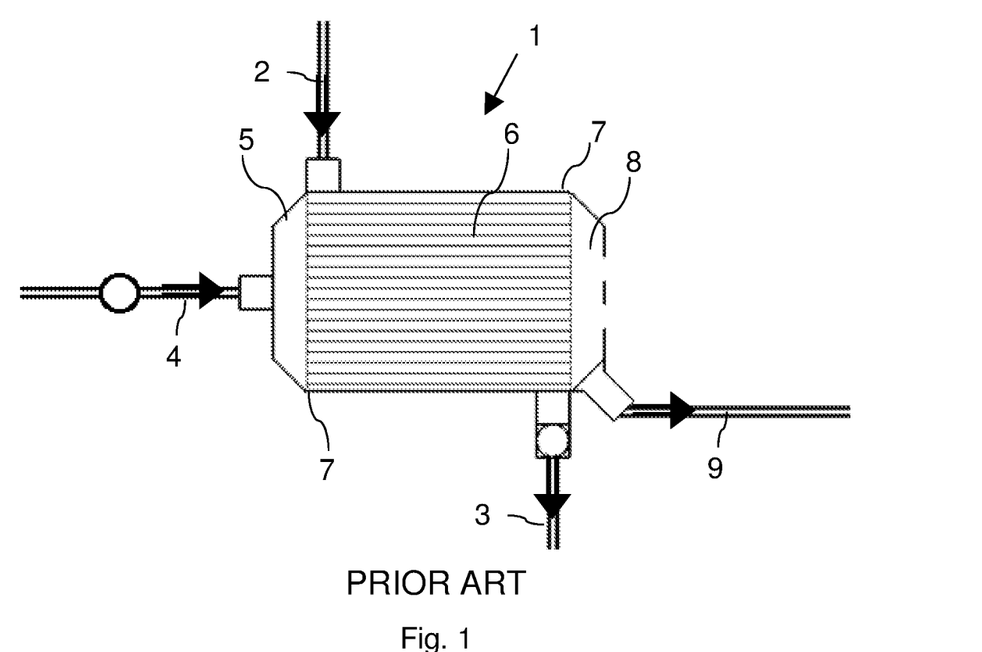
FIG. 1 shows a prior art oxygenator arrangement.

FIG. 1 shows elements expected to be found in a known oxygenator 1 used in extracorporeal ventilation. The oxygenator 1 is provided to expose oxygen-reduced, or venous, blood to a gas supply comprising oxygen and a low percentage of carbon dioxide. The carbon dioxide percentage in the supplied gas may be practically 0. During a gas exchange between the blood and the gas supply the blood is oxygenated and carbon dioxide is removed in order to provide oxygen-enriched and carbon dioxide reduced arterial blood. The oxygenator 1 comprises a blood passage comprising blood inlet 2 via which venous blood is supplied into the oxygenator 1 and a blood outlet 3 via which outgoing blood leaves the oxygenator 1 for further use, often as arterial blood to be returned to a patient. The oxygenator 1 also comprises a gas passage comprising a sweep gas supply 4 leading via an inlet chamber 5 through a gas-blood interface 7 and via an exhaust chamber 8 to an exhaust passage 9.

Modern gas-blood interfaces typically comprise a bundle of several thousand hollow, micro-porous fibres with micro-porous, gas-permeable properties. The sweep gas is supplied through the interior, hollow space of the fibres and blood flows around the fibres and gas exchange is promoted by relative gas-transfer gradients between the concentrations of oxygen and carbon dioxide in blood and gas, respectively. The hollow fibres are held together at their ends by typically a resin, so-called potting 7, which seals off the blood passage from the inlet chamber 5 and the exhaust chamber 8. The design is such that the gas flow conditions, in particular flow rate and volumes, from the inlet chamber 5 through the gas-blood interface 6 are, as much as is controllable, expected to be homogeneous, as would be expected from a single, static gas supply port. It will be understood that, in operation, the gas composition and pressure will change along the hollow fibres from the inlet-facing potting 7 towards outlet-facing potting 7, because the oxygen content is gradually reducing as blood picks up oxygen molecules, and the carbon dioxide content is gradually increasing due to diffusion from blood carbon dioxide into the oxygenation gas. However, for a given distance from the inlet chamber 5, the gas flow conditions through the hollow fibres are determined by parameters of the sweep gas supply 4 and are practically homogeneous.

The aim of such an oxygenator type is to modulate the partial pressure of oxygen PaO2 in the outgoing blood. The aim may also be to modulate the partial pressure of carbon dioxide PaCO2 in the outgoing blood. PaO2 may be modulated by adjusting the oxygen percentage (ie partial oxygen pressure) of the oxygenation gas, the remaining component being mainly nitrogen. PaCO2 may be modulated by adjusting the flow rate of the oxygenation gas. Using an oxygenation gas supply system such as described in WO2016/087859 and WO2016/087861 by the present applicant, both the composition and the flow rate of the oxygenation gas can be controlled simultaneously, allowing both the PaO2 and PaCO2 that is expected in the outgoing blood to be modulated simultaneously.

Figure 2:
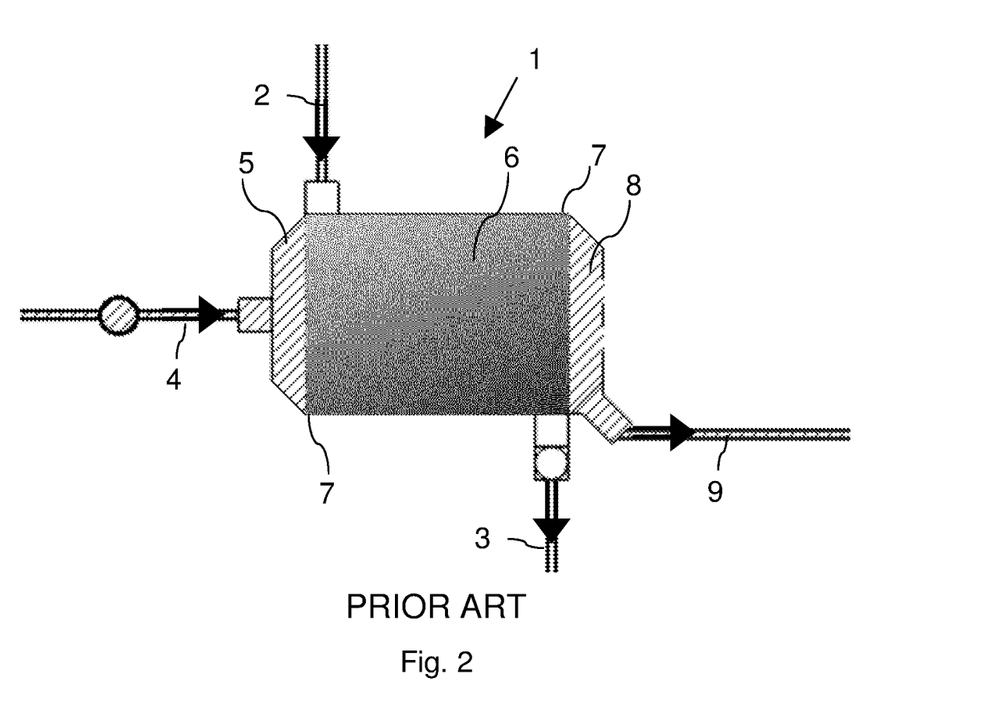
FIG. 2 illustrates a gas-transfer gradient expected during operation of a FIG. 1 device.

FIG. 2 illustrates, schematically, the carbon dioxide gas-transfer gradient of an oxygenator 1 in use. The same numerals are used in FIGS. 2 and 1 for the same components, and the description of the same components is not repeated where this corresponds to FIG. 1. The exchange of blood gas with supplied gas components is driven by a gradient across the membrane (from the inside of the hollow fibres towards the outside of the hollow fibres). The higher the gradient, the more effective the gas transfer. FIG. 2 illustrates the gradient that drives the transfer of carbon dioxide from the blood to the gas passage. As venous blood enters via blood inlet 2, in the reading orientation of FIG. 2 in the top left corner, the blood has a relatively high partial pressure of carbon dioxide. Upon entering the gas-blood interface the blood is exposed to fresh supply gas from the sweep gas supply 4 with a carbon dioxide partial pressure of practically nil. Initially, there is a high gas-transfer gradient causing carbon dioxide transfer into the gas passage. As the blood flows through the gas-blood interface 6 towards the blood outlet 3 (flowing down in the reading orientation of FIG. 2), the blood carbon dioxide decreases and so the gas-transfer gradient decreases relative to the supply gas. Furthermore, along the gas passage (in the reading orientation of FIG. 2, from the inlet chamber 5 on the left to the exhaust chamber 8 on the right), the partial pressure of carbon dioxide in the supply gas increases and so the gas-transfer gradient decreases. In summary, the gas-transfer gradient decreases across the gas-blood interface (a) in the direction of the blood flow path (b) in the direction of the gas passage. The carbon dioxide gas-transfer gradient is schematically indicated by lighter and darker dithering within the gas-blood interface 6; a lighter dithering indicates a gas-transfer gradient, more likely to promote removal of carbon dioxide from the blood. A darker dithering indicates a lower gas-transfer gradient, with a slower carbon dioxide removal rate than a light dithering area.

Figure 3:
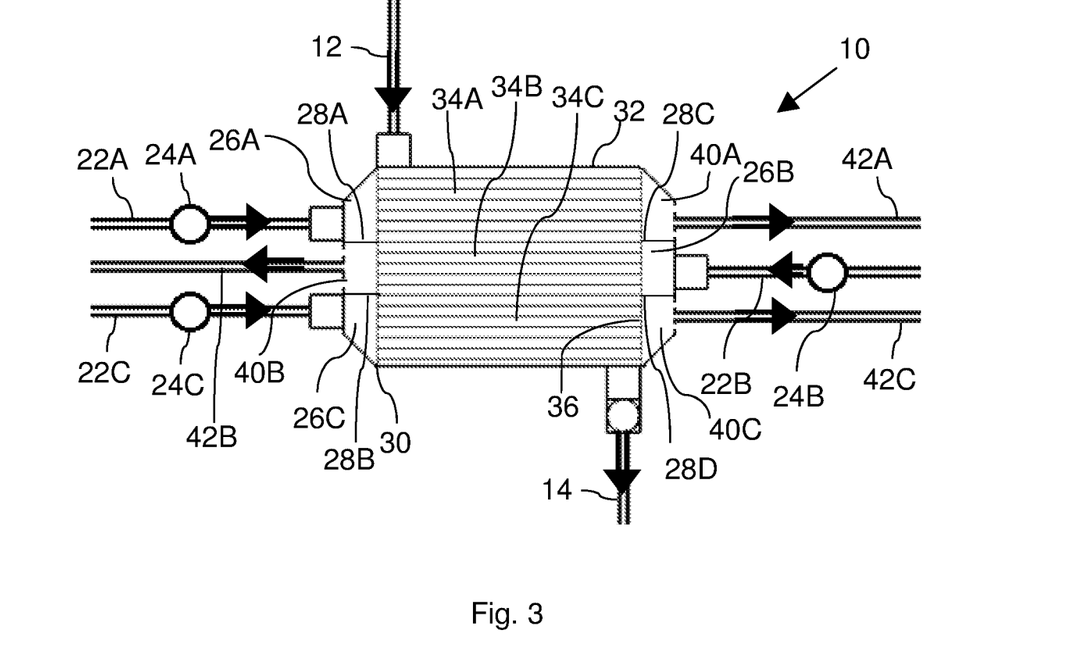
FIG. 3 is a schematic illustration of a blood gas management device.

FIG. 3 shows an oxygenator 10 in accordance with embodiments of the invention. The oxygenator 10 comprises a blood inlet 12 and a blood outlet 14 providing a blood passage through the oxygenator 10. The oxygenator 10 comprises a gas-blood interface 32 in which a plurality of hollow fibres are provided which are held together as bundle by potting 30 at one end and by potting 36 at the other end. Within the oxygenator 10, the space outside the potting 30,36 of the gas-blood interface 32 provides gas chambers, one on each side of the gas-blood interface. Each gas chamber provides a gas passage with the gas-blood interface 32.

The oxygenator 10 comprises three gas paths, each of which leads via a gas supply towards a gas chamber, through the gas passages of the gas-blood interface, and via the opposite gas chamber into an exhaust line.

The first gas path comprises a first sweep gas supply 22A with a first sweep gas flow controller 24A to provide supply gas towards the gas-blood interface 32. The first gas path leads via a first inlet compartment 26A in the first gas chamber through potting 30 into the gas-blood interface 32, in particular into a first group 34A of hollow fibres, and from the gas-blood interface 32 through the potting 36 into a first exhaust compartment 40A of the second gas chamber, from where exhaust gas is removed via a first exhaust line 42A.

The second gas path corresponds in sequence to the first gas path and its integers are provided with a suffix "-B" instead of "-A". The second gas path extends in the opposite direction of the first gas path and comprises a second sweep gas supply 22B with a second sweep gas flow controller 24B to provide supply gas towards the gas-blood interface 32. The second gas path leads via a second inlet compartment 26B, which, due to the opposite orientation of the second gas path, is in the second gas chamber, through potting 36 into the gas-blood interface 32, in particular into a second group 34B of hollow fibres, and from the gas-blood interface 32 through the potting 30 into a second exhaust compartment 40B which is in the first gas chamber, from where exhaust gas is removed via a second exhaust line 42B.

The third gas path corresponds in sequence and direction to the first gas path and its integers are provided with a suffix "-C" instead of "-A". The third gas path extends parallel to the first gas path and in the opposite direction of the second gas path, and comprises a third sweep gas supply 22C with a third sweep gas flow controller 24C to provide supply gas towards the gas-blood interface 32. The third gas path leads via a third inlet compartment 26C in the first gas chamber, through potting 30 into the gas-blood interface 32, in particular into a third group 34C of hollow fibres, and from the gas-blood interface 32 through the potting 36 into a third exhaust compartment 40C in the second gas chamber, from where exhaust gas is removed via a third exhaust line 42C.

The oxygenator 10 comprises a housing that is gas tight at the gas inlet areas. In particular, the first, second and third inlet compartments 26A, 26B and 26C are gas tight to avoid contamination of the supply gas before this enters the gas-blood interface 32. At the other end, the first, second and third exhaust compartments 40A, 40B and 40C the housing may comprises several openings to allow pressure equilibration with the environment, in order to avoid a pressure build-up within the gas-blood interface 32.

The blood passage between the blood inlet 12 and the blood outlet 14 is provided by the gas-blood interface 32 bounded by the inlet-facing potting 30 and the outlet-facing potting 36, and constituted by the space inside the potting surrounding the hollow fibres 34.

Within the gas chambers, the oxygenator 10 comprises a plurality (here: four) of partitions 28, namely partitions 28A, 28B, 28C and 28D. The partitions 28 separate each of the two gas chambers into a plurality (here: three) gas compartments. At one end of the oxygenator 10, the first gas chamber is separated by two partitions 28A and 28B into the first inlet compartment 26A, the second exhaust compartment 40B, and the third inlet compartment 26C. At the other end of the oxygenator 10, the second chamber is separated by two partitions 28C and 28D into the first exhaust compartment 40A, the second inlet compartment 26B, and the third exhaust compartment 40C.

Each compartment 26A, 26B, 26C and 40A, 40B, 40C can be considered as adjoining a different portion of the potting 30 or 36, respectively. As such, each gas inlet compartment and each gas exhaust compartment has a different border with the gas-blood interface 32. The arrangement allows known oxygenator hollow fibre designs to be utilised, by addition of partitions, for a counter flow gas supply. It will be appreciated that the FIG. 3 arrangement provides a plurality (here: three) gas paths, or a plurality of groups of gas passages, crossing different regions of the same blood pathway. This facilitates providing a sterile blood passage.

The hollow fibre bundles that connect to the first inlet compartment 26A are supplyable by the first sweep gas supply 22A, and likewise, the fibres connecting to the second inlet compartment 26B are supplyable by the second sweep gas supply 22B, and the fibres connecting to the third inlet compartment 26C are supplyable by the second sweep gas supply 22C.

The partitions 28A-28D is illustrated in a fixed position in FIG. 3. The partitions 28A-28D may be fixed in position, e.g. according to an oxygenator design. The partitions 28A-28D may be re-positionable at different locations. A re-positionable partition allows the number of fibres to be changed that may be supplied via the first gas passage, the second gas passage, or the third gas passage. Furthermore, re-positionable partitions facilitate the alignment of the gas inlet compartment with its corresponding gas exhaust compartment. The partitions 28A-28D may be moveable across the potting 30 and 36. This allows the ratio of the number, and thereby the area of, the groups of hollow fibres 34A, 34B and 34C relative to each other to be altered.

The partitions 28A-28D may not necessarily have to seal against the potting 30 and/or 36 because a small amount of gas seeping into the respective other area (for instance from the first gas inlet compartment 26A into the second group of hollow fibres 34B) may be tolerable. Also, the hollow fibres are densely packed, and the edge of a partition may be larger than a hollow fibre diameter. An edge of a partition in contact with the inlet-facing potting 30 or 36 may cover a certain amount of hollow fibres such that partition-covered hollow fibres are not practically supplyable with gas. Conversely, if a partition 28 is not in close contact with the respective potting 30 or 36, hollow fibres just beneath the partition may not be supplied by sweep gas and, instead, the sweep gas may be sucked around the partition into an adjoining exhaust compartment.

Each sweep gas supply 22A, 22B and 22C is controllable separately by the respective sweep gas flow controllers 24A, 24B and 24C. Each sweep gas supply may be controllable separately. The sweep gas is understood to have a composition in which it is intended to be supplied to the gas-blood interface.

The exhaust compartments 40A, 40B and 40C may comprise one or more openings to the outside, such as slits in the housing of the oxygenator 10. The openings provide auxiliary vents which provide a mechanism against over-pressurising the gas passage.

Figure 4:
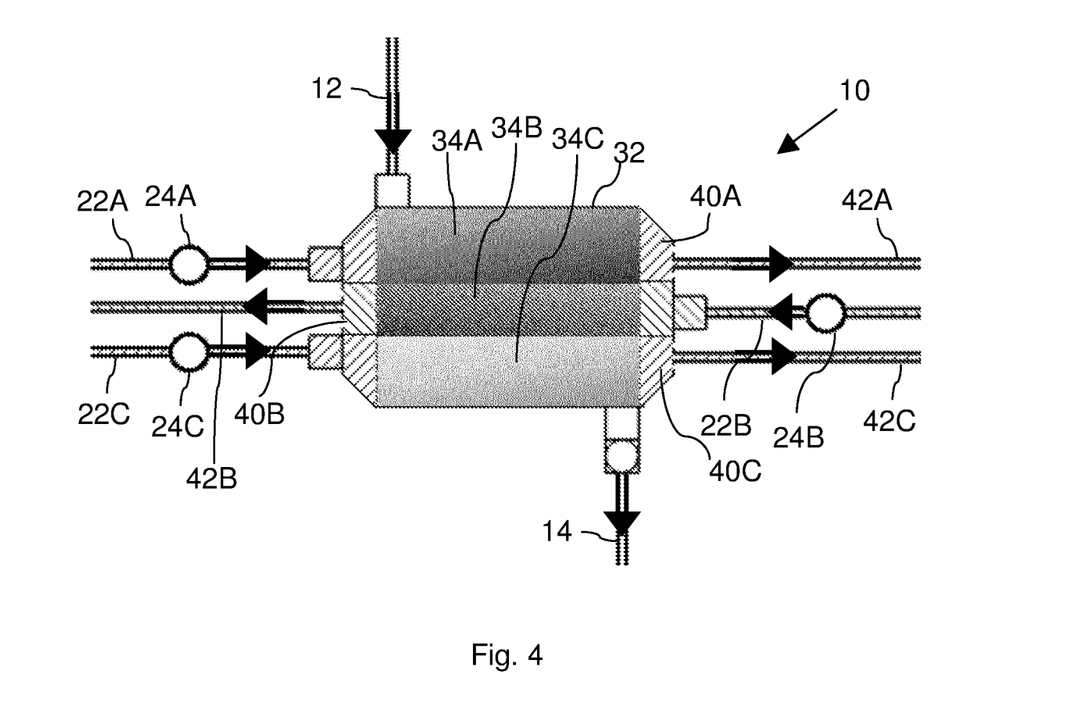
FIG. 4 illustrates gas-transfer gradients expected in one mode of operation of a FIG. 3 device.

FIG. 4 illustrates, schematically, the carbon dioxide gas-transfer gradient of an oxygenator 10 in use. The same numerals are used in FIGS. 4 and 3 for the same components, and the description of the same components is not repeated where this corresponds to FIG. 3. Similarly to FIG. 2, the carbon dioxide gas-transfer gradient is indicated by lighter and darker dithering within the gas-blood interface 32; a lighter dithering indicates a higher carbon dioxide gas-transfer gradient, more likely to promote carbon dioxide removal from the blood. A darker dithering indicates a lower gas-transfer gradient, with a slower carbon dioxide removal rate than a light dithering area.

As in FIG. 2, the gas-transfer gradient in FIG. 4 decreases across the gas-blood interface (a) in the direction of the blood flow path (b) in the direction of gas flow in a gas passage. However, in contrast to FIG. 2, due to the presence of three gas paths in counter flow in the FIG. 4 arrangement, blood flowing past the first group 34A of hollow fibres near the exhaust compartment 40A comes into contact with the second group 34B of hollow fibres that is supplied by a 'fresh' supply gas with low carbon dioxide percentage. The carbon dioxide percentage of the supply gas may be practically zero and so the diffusion gradient is relatively larger for subsequent gas paths, which is illustrates in FIG. 4 by a lighter dithering near the second inlet compartment 26B. After passing multiple (here: three) gas passages in counter flow, the blood exiting at blood outlet 14 has a lower partial pressure of carbon dioxide compared to the same number of hollow fibres in the FIG. 2 comparison.

As illustrated in FIG. 4, the multiple gas passages are in counter flow relative to each other and cross the blood passage successively, in series, such that blood flows past each of the gas passages between the blood inlet 12 and the blood outlet 14.

Note that the number of hollow fibres of the comparison in FIG. 1 and the embodiment of FIG. 3 may be identical. Indeed it is envisaged that the invention may be used with known hollow fibre interface designs. The FIG. 3 embodiment achieves a better carbon dioxide removal than the FIG. 1 comparison by way of providing supply gas from different directions relative to the blood flow path.

It will be understood that the supply gas condition, flow rates and composition are set so as to achieve, for a given blood gas management device, a set blood gas composition in the outgoing blood at the blood outlet 14.

The blood gas management device may be used to set one or more blood gas values simultaneously. For instance, the system may be used to set the partial pressures of oxygen and/or carbon dioxide simultaneously. The system provides the option to modulate the supply gas condition of each gas supply separately. In embodiments, two or more supply gas lines may be supplied by the same source of gas and distributed to the gas-blood interface via a manifold. For instance, the supply gas may have the same composition, supplied by a common source, and the flow rate through each passage is modulated separately.

Likewise, the exhaust gas removal may be carried out for each gas passage separately, or using a common exhaust gas extraction source for two or more gas passages.

Figure 5:
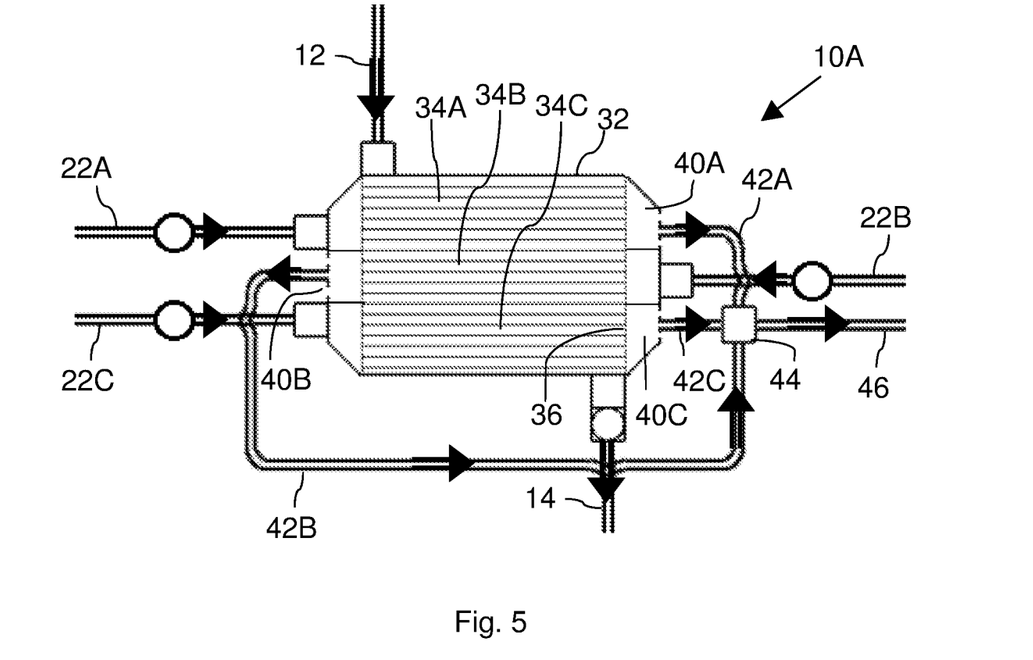
FIG. 5 is a schematic illustration of another blood gas management device.

FIG. 5 illustrates a variant of FIG. 3. The same numerals are used in FIGS. 5 and 3 for the same components, and the description of the same components is not repeated where this corresponds to FIG. 3. In the FIG. 5 arrangement the three exhaust lines 42A, 42B and 42C lead into a manifold 44 from which exhaust gases are removed via a common exhaust line 46.

Figure 6:
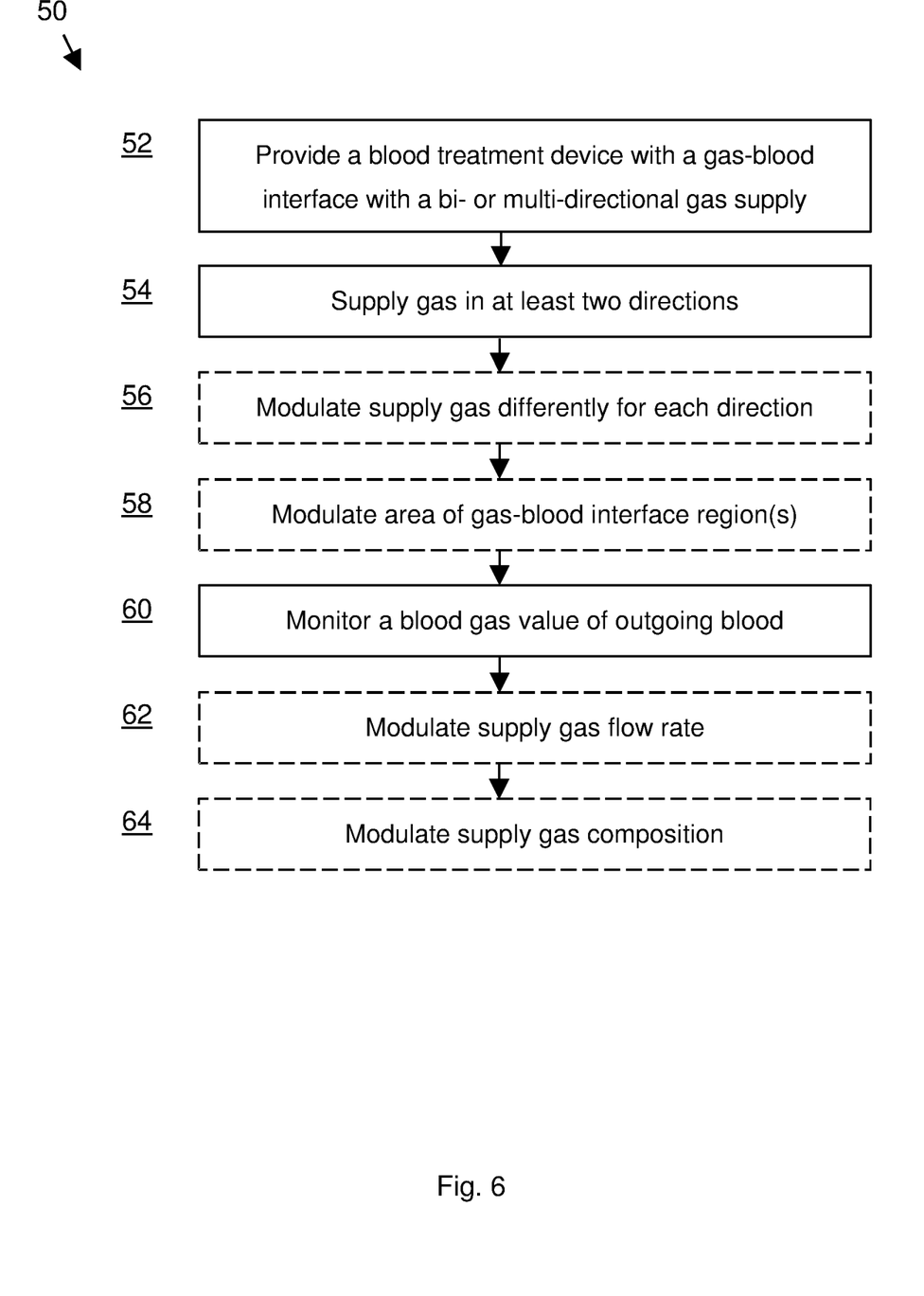
FIG. 6 shows steps of a sequence of a blood gas management method.

FIG. 6 illustrates a method 50 of managing the transfer of blood gas. The method 50 comprises a step 52 of providing a blood treatment device such as the device 10 or 10A of FIG. 3 or 5, which comprises a gas-blood interface and a configuration to supply gas from two or more directions relative to the direction of the blood flow path. In step 54, supply gas is provided to cross the blood flow path in at least two directions. In an optional step 56, the supply gas is modulated differently for at least one of the directions than for another one of the directions. In an optional step 58, the available gas-blood interface region is modulated, for instance by stopping supply of gas through one or more of the gas passages. In optional step 60, a blood gas value of the outgoing blood is measured. In optional steps 62 and 64, gas parameters are altered in response to the outgoing blood value. Such a mechanism may be used to provide a closed loop control. In optional step 62, the flow rate of one or more of the gas supplies is modulated. In optional step 64, the composition of one or more of the gas supplies is modulated.

The arrangements described herein allow the use of a single hollow fibre assembly to be used as interface with multiple gas passages. The individual gas passages are defined by partitions in the gas chambers outside the hollow fibre interface. This facilitates providing a sterile environment for the blood passage, whereby blood has to be channelled through only a single blood treatment device.

While the invention has been devised with the ability to utilise existing fibre membrane interface geometries, initial calculations indicate that the invention may be even more effective in different interface geometries. Particularly if used for carbon dioxide removal from blood, the carbon-dioxide removing effect can be maintained with longer gas passages, which allows fewer fibres to be used to achieve the same surface area of the gas-blood interface. In turn, this allows much shorter blood passages to be used, which firstly reduces the mechanical strain otherwise exerted on blood cells due to the shorter travel distance for the blood, but furthermore reduces the driving pressure otherwise required to push the blood past the otherwise many thousand fibres. A shorter blood path reduces the pumping power required to drive blood through the blood gas treatment device, which allows much smaller pumps to be used.

It is therefore believed that the invention enables much smaller blood gas treatment devices, with longer gas passages than would be practical for mono-directional gas supply systems, yet with a shorter blood passage with fewer fibres to provide the same gas-blood interface area. The invention may enable wearable, even implantable blood gas treatment devices.

In embodiments, the blood gas treatment device may comprise gas passages that within the gas-blood interface comprise at least double the length of the blood passage, or whose length is a more than 3×, 4×, 5×, the length of the blood passage measured, wherein the length of a gas passage is measured from the inlet of the gas-blood interface to the exhaust end of the gas-blood interface and the length of the blood passage is the direct distance from the blood inlet into the gas-blood interface to the blood outlet from the gas-blood interface.

The specific embodiments have been described with three gas flow paths. This arrangement has been found in calculations to provide a good trade-off between improving a gas-transfer gradient and the complexity of the system. Fewer or more than three gas flow paths may be provided.

The specific embodiments have been described as a counter flow arrangement. Such an arrangement is practical because it allows existing hollow-fibre interface geometries to be utilised. It will be understood that other gas distribution arrangements may be used, such as gas paths perpendicular to each other.

Furthermore, the specific embodiments have been described with linear gas flow paths. Oxygenators may comprise more complex blood flow and gas flow geometries.

The invention is described in relation to a blood gas management device. The blood gas management device may be part of a blood gas management system. For instance, the blood gas management system may comprise components for conditioning the supply gas and for providing the supply gas towards the blood gas management device. The blood gas management system may comprise components for removing exhaust gas.

The blood gas management system may comprise sensor arrangements and controllers to execute a closed loop control of the flow rates. Sensors may be arranged to measure values at the gas inlet and/or gas outlet of each gas path, in particular at the gas inlet and/or gas outlet of an interface gas passage. Sensors may be arranged to measure blood values before and after a gas flow path. For instance, one or more sensors may be arranged to measure blood values at the blood inlet, before the blood passes the first gas path, between two gas paths, and/or at the blood outlet, after the blood has passed all gas paths.

The invention claimed is:

1. A blood gas management device comprising:
   a plurality of gas passages each comprising a gas inlet and a gas outlet, the blood gas management device being arranged to allow a flow of a supply gas from the gas inlets through the gas passages to the gas outlets, wherein a first gas passage of the plurality of gas passages comprises a first gas inlet in the direction of a second gas outlet of a second gas passage of the plurality of gas passages, the first gas passage being configured to direct gas in counter flow to the second gas passage;
   a blood passage arranged with a gas-blood interface with the gas passages, wherein the blood gas management device is arranged to allow a flow of blood in a blood flow path through the blood passage to thereby permit an exchange of blood gas with the supply gas via the gas-blood interface; and
   a supply gas distribution arrangement configured to provide fresh supply gas from a supply gas source to each of the first gas inlet of the first gas passage and a second gas inlet of the second passage, the supply gas distribution arrangement being further configured to provide (i) a first flow of fresh supply gas into the first gas inlet and through the first gas passage in a first direction, and (ii) a second flow of fresh supply gas into the second gas inlet and through the second gas passage in a second direction, the second direction being substantially opposite to the first direction,
   wherein the first gas passage and the second gas passage are arranged in series relative to the blood flow path.

2. The blood gas management device according to claim 1, wherein the supply gas distribution arrangement is configured to provide a first supply of gas to cross at least part or all the blood flow path in the first direction and to provide a second supply of gas to cross at least part or all the blood flow path in the second direction different from the first direction.

3. The blood gas management device according to claim 1, further comprising an exhaust removal system configured to extract exhaust gas from gas outlets in different directions relative to the flow of blood.

4. The blood gas management device according to claim 3, wherein the exhaust gas removal system comprises a common connection to different gas outlets of the gas passages.

5. The blood gas management device according to claim 1, wherein at least some or all of the gas passages are provided by hollow fibres comprising gas-permeable walls.

6. The blood gas management device according to claim 1, comprised in an extracorporeal oxygenator with a gas chamber at each end of the gas passages, wherein each gas chamber is separated into a plurality of compartments, each compartment allowing gas to be directed via a separate group of gas passages.

7. The blood gas management device according to claim 1, comprising a gas sensor arrangement configured to measure at least one property of a supply gas entering the gas inlet and/or exiting the gas outlet, wherein the at least one property of the supply gas comprises one or more of: a gas flow rate; a gas pressure; and/or a percentage of carbon dioxide, oxygen and/or nitrogen in the supply gas.

8. The blood gas management device according to claim 1, comprising a blood sensor arrangement configured to measure at least one property of the blood entering and/or exiting the gas-blood interface, wherein the at least one property of the blood comprises one or more of: a blood flow rate; a blood pressure; a blood temperature and/or a percentage of carbon dioxide, oxygen and/or nitrogen in the blood.

9. The blood gas management device according to claim 1, comprising a supply gas control system configured to:
   receive as input one or more measured properties of the blood or one or more measured properties of the supply gas: and
   modulate at least one gas flow parameter in response to the one or more measured properties of the supply gas and/or the one or more measured properties of the blood, wherein the at least one gas flow parameter comprises a composition and/or a flow rate of the supply gas.

10. The blood gas management device according to claim 9, wherein the at least one measured property of the supply gas comprises one or more of: a gas flow rate; a gas pressure; and/or a percentage of carbon dioxide, oxygen and/or nitrogen in the supply gas.

11. The blood gas management device according to claim 9, wherein the at least one measured property of the blood comprises one or more of: a blood flow rate; a blood pressure; a blood temperature; and/or a percentage of carbon dioxide, oxygen and/or nitrogen in the blood.

12. The blood gas management device according to claim 1, wherein the plurality of gas passages is part of an oxygenator or of a carbon dioxide management device.

13. A method of using a blood gas management device comprising a plurality of gas passages each comprising a gas inlet and a gas outlet, and a blood passage having a gas-blood interface with the gas passages, wherein a first gas passage of the plurality of gas passages comprises a first gas inlet in the direction of a second gas outlet of a second gas passage of the plurality of gas passages, the first gas passage being configured to direct gas in counter flow to the second gas passage, and wherein the first gas passage and the second gas passage are arranged in series relative to a blood flow path through the blood passage, the method comprising:

directing a flow of supply gas from the gas inlets through the gas passages to the gas outlets, wherein directing the flow of supply gas includes directing ci) a first flow of fresh supply gas from a supply gas source into the first gas inlet and through the first gas passage in in a first direction, and (ii) a second flow of fresh supply gas from the supply gas source into a second gas inlet of the second gas passage and through the second gas passage in a second direction, the second direction being substantially opposite to the first direction; and     allowing a flow of blood in the blood flow path to permit an exchange of blood gas with the supply gas via the gas-blood interface.

14. The method according to claim 13, comprising providing a first supply of gas to cross at least part or all the blood flow path in the first direction and providing a second supply of gas to cross at least part or all the blood flow path in the second direction different from the first direction.

15. The method according to claim 13, comprising extracting exhaust gas from gas outlets in different directions relative to the flow of blood.

16. The method according to claim 15, further comprising extracting the exhaust gas using a common exhaust gas removal system connected to the gas outlets of the plurality of gas passages.

17. The method according to claim 13, used in an extracorporeal oxygenator with a gas chamber at each end of the gas passages, wherein each gas chamber is separated into a plurality of compartments, wherein the method comprises directing different supplies of gas via a separate group of gas passages.

18. The method according to claim 13, comprising using a gas sensor arrangement to obtain at least one gas value of a supply gas entering the gas inlet and/or exiting the gas outlet, wherein the at least one gas value comprises carbon dioxide, oxygen, nitrogen, and/or a combination thereof.

19. The method according to claim 13, comprising a blood sensor arrangement configured to obtain at least one blood value of the blood entering and/or exiting the gas-blood interface, wherein the at least one blood value comprises carbon dioxide, oxygen, nitrogen, or a combination thereof.

20. The method according to claim 13, comprising using a feedback loop to modulate at least one gas flow parameter in response to the gas value and/or the blood value, wherein the at least one gas flow parameter comprises a composition and/or a flow rate of the supply gas.

* * * * *